United States Patent [19]

Hashida et al.

[11] Patent Number: 5,763,383
[45] Date of Patent: Jun. 9, 1998

[54] ALKALINE LIPASES

[75] Inventors: Miyoko Hashida, Urayasu; Naoko Ikegami, Ichikawa; Masanobu Abo; Yukiko Takamura, both of Funabashi, all of Japan

[73] Assignee: Novo Nordisk A/S, Bagsvaerd, Denmark

[21] Appl. No.: 436,440

[22] PCT Filed: Dec. 22, 1993

[86] PCT No.: PCT/DK93/00442

§ 371 Date: May 23, 1995

§ 102(e) Date: May 23, 1995

[87] PCT Pub. No.: WO94/14940

PCT Pub. Date: Jul. 7, 1994

[30] Foreign Application Priority Data

Dec. 22, 1992 [DK] Denmark ................. 1529/92
Jan. 28, 1993 [DK] Denmark ................. 96/93
Apr. 20, 1993 [DK] Denmark ................. 442/93

[51] Int. Cl.[6] .................. C11D 3/386; C12N 9/20
[52] U.S. Cl. .................. 510/392; 510/530; 435/198
[58] Field of Search ............... 252/174.12, DIG. 12; 435/198; 510/392, 530

[56] References Cited

U.S. PATENT DOCUMENTS

| | | | |
|---|---|---|---|
| 3,317,400 | 5/1967 | Reusser | 192/2 |
| 3,431,175 | 3/1969 | Arima | 195/62 |
| 3,684,658 | 8/1972 | Delin | 195/62 |
| 3,888,737 | 6/1975 | Watanabe et al. | 195/28 R |
| 4,347,184 | 8/1982 | Kojima | 260/316 |
| 5,030,278 | 7/1991 | Venegas | 252/174.12 |
| 5,173,417 | 12/1992 | Takeda et al. | 435/198 |
| 5,240,851 | 8/1993 | Paridans | 435/253.3 |
| 5,244,798 | 9/1993 | Takeda et al. | 435/198 |

FOREIGN PATENT DOCUMENTS

| | | |
|---|---|---|
| WO 89/01032 | 2/1989 | WIPO. |
| 9414940 | 7/1994 | WIPO. |

OTHER PUBLICATIONS

Daza et al., Mol. Gen. Genet., vol. 222, pp. 384–392 (1990).
Sztajer et al., Enzyme Microb. Technol., vol. 10, pp. 492–497 (1988).
Hou et al., JAOCS, vol. 69, No. 11, pp. 1088–1097 (1992).
Bormann et al., Dechema Monographies (237–47), (1992).

*Primary Examiner*—Paul Lieberman
*Assistant Examiner*—Kery A. Fries
*Attorney, Agent, or Firm*—Steve T. Zelson; Elias J. Lambiris

[57] ABSTRACT

A highly alkaline, positionally non-specific lipase can be obtained from the strains of streptomyces, cluster 1. Strains of cluster 1 of Streptomyces were not previously known to produce lipase. The lipase preparation has more than 50% of its optimum activity at pH 10 and is useful, e.g. in detergents.

32 Claims, 9 Drawing Sheets pH PROFILE OF LB 501 LIPASE

FIG. 4 pH PROFILE OF LB 512 LIPASE

FIG.6 pH PROFILE OF ATCC 23899 LIPASE

FIG. 8A
LB502 LIPASE

FIG. 8B
LIPOLASE

LATROSCAN CHROMATOGRAMS

1
ALKALINE LIPASES

CROSS-REFERENCE TO RELATED APPLICATIONS

This application is a PCT of PCT/DK93/00442 filed Dec. 22, 1993, which is incorporated herein by reference.

TECHNICAL FIELD

This invention relates to a novel positionally non-specific, alkaline lipase which is useful, e.g., in detergents. The invention also relates to a method of producing the novel lipase and to a detergent composition comprising the novel lipase.

BACKGROUND ART

Within the last 5 years, a microbial lipase derived from the fungus *Humicola lanuginosa* has been introduced into many commercial brands of detergent in order to improve the removal of fatty stains. Other microbial lipases have also been suggested for use in detergents, e.g. bacterial lipase from *Pseudomonas cepacia* (U.S. Pat. No. 4,876,024).

Many detergents are alkaline with a high pH in solution (e.g. around pH 10) and contain a builder to bind $Ca^{++}$ ions. It is the object of this invention to provide a lipase with high activity at high pH in the absence of $Ca^{++}$. The lipase should be positionally non-specific to be able to hydrolyze all ester bonds in triglycerides.

SUMMARY OF THE INVENTION

Surprisingly, we have found that a highly alkaline, positionally non-specific lipase can be obtained from strains of Streptomyces, cluster 1. Strains of cluster 1 of Streptomyces were not previously known to produce lipase.

Accordingly, in its first aspect, the invention provides a lipase preparation which:

(1) is positionally non-specific, (2) has an activity at pH 10 which is more than 50% of the activity at the optimum pH, when both activities are determined in a $Ca^{++}$ free assay with olive oil as substrate and polyvinyl alcohol as emulsifier at 40° C. for 20 minutes, and (3) is producible by cultivation of a strain of Streptomyces cluster 1.

In another aspect, the invention provides a lipase which:

(1) is positionally non-specific, (2) has optimum activity at a pH in the range 9–11, when determined with olive oil as substrate and polyvinyl alcohol as emulsifier at 40° C. for 20 minutes, and (3) is immunologically identical with an extracellular lipase native to a strain of Streptomyces cluster 1.

In a third aspect, the invention provides a process for producing the lipase preparation of the invention, comprising cultivation of a lipase-producing strain of Streptomyces cluster 1 in a suitable nutrient medium, containing carbon and nitrogen sources and inorganic salts, followed by recovery of the desired enzyme.

In a further aspect, the invention provides a detergent composition comprising the lipase of the invention.

BRIEF DESCRIPTION OF DRAWINGS

The present invention is further illustrated by reference to the accompanying drawings, in which.

DETAILED DISCLOSURE OF THE INVENTION

Microorganisms

The microbial strain used in this invention is a bacterium of the order Actinomycetales which belongs to Streptomyces cluster 1, as defined by S. T. Williams et al., *Journal of General Microbiology* (1983), 129, 1743–1813.

Within Streptomyces cluster 1, the following subclusters, species and strains are preferred. Variants and mutants thereof capable of producing the lipase described above may also be used in the invention.

| Subcluster | Species | Strain |
| --- | --- | --- |
| 1A | *S. albidoflavus* | |
|  | *S coelicolor* | ATCC 23899 |
|  |  | FERM BP-4236 |
|  |  | FERM BP-4237 |
|  | *S. limosus* | ATCC 19778 (Type strain) |
| 1B | *S. alboviridis* | ATCC 25425 (Type strain) |
|  | *S. griseus* | ATCC 23345 (Type strain) |
|  |  | DSM 7349 |
|  |  | DSM 7350 |
|  |  | DSM 8672 |
|  | *S. parvus* | ATCC 12433 (Type strain) |
|  | *S. setonii* | ATCC 25497 (Type strain) |
| 1C | *S. nitrosporeus* | ATCC 12769 (Type strain) |

The above-mentioned ATCC strains are freely available from the American Type Culture Collection, 12301 Parklawn Drive, Rockville, Md., USA.

The following strains have been deposited by the inventors under the terms of the Budapest Treaty on the International Recognition of the Deposits of Microorganisms for the Purpose of Patent Procedures. The strains were classified as shown below.

| Taxonomic designation | Deposit No. | Deposit date | Depositor's designation |
| --- | --- | --- | --- |
| *S. griseus* | DSM 7349 | 10 December 1992 | LB 501 |
| *S. griseus* | DSM 7350 | 10 December 1992 | LB 502 |
| *S. griseus* | DSM 8672 | 2 November 1993 | LB 524 |
| *S. coelicolor* | FERM BP-4236 | 10 March 1993 | LB 511 |
| *S. coelicolor* | FERM BP-4237 | 10 March 1993 | LB 512 |

Here, DSM indicates a deposit made at Deutsche Sammlung von Mikroorganismen und Zellkulturen (DSM), Mascheroder Weg 1b, 3300 Braunschweig, Germany. FERM indicates a deposit made at the National Institute of Bioscience and Human-Technology (NIBHT), Agency of Industrial Science and Technology, Ministry of International Trade and Industry, 1-3, Higashi 1-chome, Tsukuba-shi, Ibaragi-ken 305, Japan.

Positional Specificity of Lipase

The positional specificity of a lipase may be checked by partial hydrolysis of a triglyceride and analysis of the diglycerides formed. The lipase of this invention forms both 1,3-diglyceride and 1,2-diglyceride and is therefore positionally non-specific, i.e. it reacts with all three ester bonds in a triglyceride.

Lipase Activity at Alkaline pH

The lipase (lipolytic enzyme) provided by the invention is highly alkaline. It is characterized by having more than 50% (preferably more than 80%) of its optimum activity at pH 10, when determined in the absence of $Ca^{++}$ with olive oil as substrate and polyvinyl alcohol as emulsifier at 40° C. for 20 minutes.

Alternatively, it can be characterized by having optimum activity of 9 or more, when determined with olive oil as substrate and polyvinyl alcohol as emulsifier at 40° C. for 20 minutes. Preferably, the pH optimum is in the range 9–11, e.g. at a pH of 9.5 or more, most preferably at a pH of 10 or more, e.g. in the range of from pH 9.5 to pH 10.5.

Lipase Activity in the Presence of Detergent

Preferred lipases of the invention retain high activity in the presence of a detergent. They can be characterized by having an activity in a detergent solution at pH 10.2 which is more than 50% of the activity in glycine or diethanol amine buffer at pH 10, when both activities are measured with olive oil as substrate at 60 minutes reaction time, and the detergent solution consists of 0.35 g/l linear alkyl benzene sulfonate, 0.15 g/l alcohol ethoxylate, 1.25 g/l sodium tripolyphosphate, 1.00 g/l sodium sulfate, 0.45 g/l sodium carbonate and 0.15 g/l sodium metasilicate.

Alternatively, the preferred lipases can be characterized by having an activity in a detergent solution at pH 7.5 which is at least 75% of the activity in buffer at the same pH, when both activities are measured with p-nitrophenyl butyrate as the substrate at 40° C. and 30 minutes reaction time, the buffer is 0.2M Tris-HCl, and the detergent solution is 0.1% alcohol ethoxylate or linear alkyl sulfonate.

A lipase having the indicated activity in a detergent solution can be obtained from Streptomyces subcluster 1 A or 1 B, e.g. the species *S. griseus*, *S. coelicolor* or *S. parvus*, particularly the strain *S. griseus* DSM 7349, DSM 7350, DSM 8672, *S. coelicolor* FERM BP-4236, FERM BP-4237, ATCC 23899 or *S. parvus* ATCC 12433.

Lipase Activity in the Absence of $Ca^{++}$

In a particularly preferred embodiment, the lipase of the invention has an activity in the absence of $Ca^{++}$ of more than 50% of the activity at 50 mM $Ca^{++}$ when both activities are measured by the olive oil/PVA method described below.

A microbial strain capable of producing a lipase having the stated activity in the absence of $Ca^{++}$ is novel and is provided by the invention. A preferred strain is *S. griseus* DSM 7350.

Immunochemical Properties

Positionally non-specific lipases having immunochemical properties identical or partially identical to those of an extracellular lipase native to a strain of Streptomyces cluster 1 and having the stated activity at high pH are within the scope of the invention. The immunochemical properties can be determined by immunological cross-reaction identity tests. The identity tests can be performed by the well-known Ouchterlony double immunodiffusion procedure or by tandem crossed immunoelectrophoresis according to I. M. Roitt; Immunology, Gower Medical Publishing (1985) and N. H. Axelsen; Handbook of Immunoprecipitation-in-Gel Techniques, Blackwell Scientific Publications (1983). Chapters 5 and 14. The terms immunochemical identity (antigenic identity) and partial immunochemical identity (partial antigenic identity) are described in Axelsen, supra, Chapters 5, 19 and 20 and Roitt, supra, Chapter 6.

Monospecific antiserum for use in immunological tests can be raised, e.g. in rabbits, against a purified lipase, e.g. as described in Chapter 41 of N. H. Axelsen, supra or Chapter 23 of N. H. Axelsen et al., A Manual of Quantitative Immunoelectrophoresis, Blackwell Scientific Publications (1973).

Lipase Activity Determination

The lipase activity is determined using olive oil emulsified with polyvinyl alcohol as substrate (olive oil and 2% PVA solution in volume ratio 1:3; PVA, n=1750±50). A mixture of 0.1 ml of lipase solution, 0.2 ml of 200 mM diethanol amine buffer, and 0.2 ml of olive oil/PVA emulsion, is stirred at 40° C. for 10 or 20 minutes. The reaction is terminated by adding 0.1 ml of 1N HCl.

After termination, 2.0 ml of a 1:1 mixture of chloroform and methanol, containing 0.1% lithocholic acid as internal standard, are added to the reaction medium, which medium is then mixed vigorously. After sedimentation, the solvent layer is removed and subjected to determination for released fatty acids by TLC-FID analysis (Iatroscan™).

Production of Lipase

The lipase of the invention may be produced by cultivation of one of the microorganisms described above in a suitable nutrient medium, containing carbon and nitrogen sources and inorganic salts, followed by recovery of the lipase.

The lipase may also be obtained by recombinant DNA-technology by methods known in the art per se, e.g. isolating a DNA fragment encoding the lipase, combining the DNA fragment with appropriate expression signal(s) in an appropriate vector, introducing the vector or parts thereof into an appropriate host (i.e. an *Escherichia coli*, a member of the genera Bacillus, Streptomyces or Saccharomyces, or is a filamentous fungus, preferably a member of the genus Aspergillus), either as an autonomously replicating plasmid or integrated into the chromosome, cultivating the host organism under conditions leading to expression of the lipase, and recovering the lipase from the culture medium.

After the cultivation, the lipase may be recovered and purified from the culture broth by conventional methods, such as hydrophobic chromatography, ion exchange chromatography and combinations thereof.

Application of Lipase

The lipase of the invention may be used in conventional applications of lipase, particularly at a high pH, e.g. in laundry and dishwash detergents, in institutional and industrial cleaning and in leather processing.

The lipase of the invention is positionally non-specific (i.e. able to hydrolyze all three ester bonds in a triglyceride) and it can also be used for the total hydrolysis of fats and oils. Suitable conditions may be pH 7, 60° C., since the lipase is more thermostable around neutral pH.

Laundry Detergent Compositions

According to the invention, the lipase may typically be a component of a detergent composition. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molar weights of 1000 to 20000, ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent composition of the invention may be in any convenient form, e.g. as powder, granules, paste or liquid. A liquid detergent may be aqueous, typically containing up to 70% water and 0–30% organic solvent, or nonaqueous.

The detergent composition comprises one or more surfactants, each of which may be anionic, nonionic, cationic, or zwitterionic. The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid or soap. It may also contain 0–40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, alkyl(N-methyl)-glucoseamide or polyhydroxy alkyl fatty acid amide (e.g. as described in WO 92/06154).

The detergent composition may additionally comprise one or more other enzymes, such as amylase, cutinase, protease, cellulase, peroxidase, and oxidase.

The detergent may contain 1–65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder.

The detergent may comprise one or more polymers. Examples are carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine (TAED) or nonanoyloxybenzenesulfonate (NOBS). Alternatively, the bleaching system may comprise peroxyacids of e.g. the amide, imide, or sulfone type.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative as e.g. an aromatic borate ester, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, or perfume.

The pH (measured in aqueous solution at use concentration) will usually be neutral or alkaline, e.g. 7–11.

Particular forms of detergent compositions within the scope of the invention include:

1) A detergent composition formulated as a granulate having a bulk density of at least 600 g/l comprising

| | |
|---|---|
| linear alkylbenzenesulfonate (calculated as acid) | 7–12% |
| alcohol ethoxysulfate (e.g. $C_{12-18}$ alcohol, 1-2 EO) or alkyl sulfate (e.g. $C_{16-18}$) | 1–4% |
| alcohol ethoxylate (e.g. $C_{14-15}$ alcohol, 7 EO) | 5–9% |
| sodium carbonate (as $Na_2CO_3$) | 14–20% |
| soluble silicate (as $Na_2O,2SiO_2$) | 2–6% |
| zeolite (as $NaAlSiO_4$) | 15–22% |
| sodium sulfate (as $Na_2SO_4$) | 0–6% |
| sodium citrate/citric acid (as $C_6H_5Na_3O_7/C_6H_8O_7$) | 0–15% |
| sodium perborate (as $NaBO_3.H_2O$) | 11–18% |
| TAED | 2–6% |
| carboxymethylcellulose | 0–2% |
| polymers (e.g. maleic/acrylic acid copolymer, PVP, PEG) | 0–3% |
| enzymes | 0–5% |
| minor ingredients (e.g. suds supressors, perfume, optical brightener, photobleach) | 0–5% |

2) A detergent composition formulated as a granulate having a bulk density of at least 600 g/l comprising

| | |
|---|---|
| linear alkylbenzenesulfonate (calculated as acid) | 6–11% |
| alcohol ethoxysulfate (e.g. $C_{12-18}$ alcohol, 1-2 EO) or alkyl sulfate (e.g. $C_{16-18}$) | 1–3% |
| alcohol ethoxylate (e.g. $C_{14-15}$ alcohol, 7 EO) | 5–9% |
| sodium carbonate (as $Na_2CO_3$) | 15–21% |
| soluble silicate (as $Na_2O,2SiO_2$) | 1–4% |
| zeolite (as $NaAlSiO_4$) | 24–34% |
| sodium sulfate (as $Na_2SO_4$) | 4–10% |
| sodium citrate/citric acid (as $C_6H_5Na_3O_7/C_6H_8O_7$) | 0–15% |
| carboxymethylcellulose | 0–2% |
| polymers (e.g. maleic/acrylic acid copolymer, PVP, PEG) | 1–6% |
| enzymes | 0–5% |
| minor ingredients (e.g. suds supressors, perfume) | 0–5% |

3) A detergent composition formulated as a granulate having a bulk density of at least 600 g/l comprising

| | |
|---|---|
| linear alkylbenzenesulfonate (calculated as acid) | 5–9% |
| alcohol ethoxylate (e.g. $C_{12-15}$ alcohol, 7 EO) | 7–14% |
| soap as fatty acid (e.g. $C_{16-22}$) | 1–3% |
| sodium carbonate (as $Na_2CO_3$) | 10–17% |
| soluble silicate (as $Na_2O,2SiO_2$) | 3–9% |
| zeolite (as $NaAlSiO_4$) | 23–33% |
| sodium sulfate (as $Na_2SO_4$) | 0–4% |
| sodium perborate (as $NaBO_3.H_2O$) | 8–16% |
| TAED | 2–8% |
| phosphonate (e.g. EDTMPA) | 0–1% |
| carboxymethylcellulose | 0–2% |
| polymers (e.g. maleic/acrylic acid copolymer, PVP, PEG) | 1–3% |
| enzymes | 0–5% |
| minor ingredients (e.g. suds supressors, perfume, optical brightener) | 0–5% |

4) A detergent composition formulated as a granulate having a bulk density of at least 600 g/l comprising

| | |
|---|---|
| linear alkylbenzenesulfonate (calculated as acid) | 8–12% |
| alcohol ethoxylate (e.g. $C_{12-15}$ alcohol, 7 EO) | 10–25% |
| sodium carbonate (as $Na_2CO_3$) | 14–22% |
| soluble silicate (as $Na_2O,2SiO_2$) | 1–5% |
| zeolite (as $NaAlSiO_4$) | 25–35% |
| sodium sulfate (as $Na_2SO_4$) | 0–10% |
| carboxymethylcellulose | 0–2% |
| polymers (e.g. maleic/acrylic acid copolymer, PVP, PEG) | 1–3% |
| enzymes | 0–5% |
| minor ingredients (e.g. suds supressors, perfume) | 0–5% |

5) An aqueous liquid detergent composition comprising

| | |
|---|---|
| linear alkylbenzenesulfonate (calculated as acid) | 15–21% |
| alcohol ethoxylate (e.g. $C_{12-15}$ alcohol, 7 EO or $C_{12-15}$ alcohol, 5 EO) | 12–18% |
| soap as fatty acid (e.g. oleic acid) | 3–13% |
| alkenylsuccinic acid ($C_{12-14}$) | 0–13% |
| aminoethanol | 8–18% |
| citric acid | 2–8% |
| phosphonate | 0–3% |
| polymers (e.g. PVP, PEG) | 0–3% |
| borate (as $B_4O_7$) | 0–2% |
| ethanol | 0–3% |
| propylene glycol | 8–14% |
| enzymes | 0–5% |
| minor ingredients (e.g. dispersants, suds supressors, perfume, optical brightener) | 0–5% |

6) An aqueous structured liquid detergent composition comprising

| | |
|---|---|
| linear alkylbenzenesulfonate (calculated as acid) | 15–21% |
| alcohol ethoxylate (e.g. $C_{12-15}$ alcohol, 7 EO or $C_{12-15}$ alcohol, 5 EO) | 3–9% |
| soap as fatty acid (e.g. oleic acid) | 3–10% |
| zeolite (as $NaAlSiO_4$) | 14–22% |
| potassium citrate | 9–18% |
| borate (as $B_4O_7$) | 0–2% |
| carboxymethylcellulose | 0–2% |
| polymers (e.g PEG, PVP) | 0–3% |
| anchoring polymers as e.g. lauryl metharylate/acrylic acid copolymer; molar ratio 25:1; MW 3800 | 0–3% |
| glycerol | 0–5% |
| enzymes | 0–5% |
| minor ingredients (e.g. dispersants, suds supressors, perfume, optical brighteners) | 0–5% |

7) A detergent composition formulated as a granulate having a bulk density of at least 600 g/l comprising

| | |
|---|---|
| fatty alcohol sulfate | 5–10% |
| ethoxylated fatty acid monoethanolamide | 3–9% |
| soap as fatty acid | 0–3% |
| sodium carbonate (as $Na_2CO_3$) | 5–10% |
| soluble silicate (as $Na_2O,2SiO_2$) | 1–4% |
| zeolite (as $NaAlSiO_4$) | 20–40% |
| sodium sulfate (as $Na_2SO_4$) | 2–8% |
| sodium perborate (as $NaBO_3.H_2O$) | 12–18% |
| TAED | 2–7% |
| polymers (e.g. maleic/acrylic acid copolymer, PEG) | 1–5% |
| enzymes | 0–5% |
| minor ingredients (e.g. optical brightener, suds supressors, perfume) | 0–5% |

8) A detergent composition formulated as a granulate comprising

| | |
|---|---|
| linear alkylbenzenesulfonate (calculated as acid) | 8–14% |
| ethoxylated fatty acid monoethanolamide | 5–11% |
| soap as fatty acid | 0–3% |
| sodium carbonate (as $Na_2CO_3$) | 4–10% |
| soluble silicate (as $Na_2O,2SiO_2$) | 1–4% |
| zeolite (as $NaAlSiO_4$) | 30–50% |
| sodium sulfate (as $Na_2SO_4$) | 3–11% |
| sodium citrate (as $C_6H_5Na_3O_7$) | 5–12% |
| polymers (e.g. PVP, maleic/acrylic acid copolymer, PEG) | 1–5% |
| enzymes | 0–5% |
| minor ingredients (e.g. suds supressors, perfume) | 0–5% |

9) A detergent composition formulated as a granulate comprising

| | |
|---|---|
| linear alkylbenzenesulfonate (calculated as acid) | 6–12% |
| nonionic surfactant | 1–4% |
| soap as fatty acid | 2–6% |
| sodium carbonate (as $Na_2CO_3$) | 14–22% |
| zeolite (as $NaAlSiO_4$) | 18–32% |
| sodium sulfate (as $Na_2SO_4$) | 5–20% |
| sodium citrate (as $C_6H_5Na_3O_7$) | 3–8% |
| sodium perborate (as $NaBO_3.H_2O$) | 4–9% |
| bleach activator (e.g. NOBS or TAED) | 1–5% |
| carboxymethylcellulose | 0–2% |
| polymers (e.g. polycarboxylate or PEG) | 1–5% |
| enzymes | 0–5% |
| minor ingredients (e.g. optical brightener, perfume) | 0–5% |

10) An aqueous liquid detergent composition comprising

| | |
|---|---|
| linear alkylbenzenesulfonate (calculated as acid) | 15–23% |
| alcohol ethoxysulfate (e.g. $C_{12-15}$ alcohol, 2-3 EO) | 8–15% |
| alcohol ethoxylate (e.g. $C_{12-15}$ alcohol, 7 EO or $C_{12-15}$ alcohol, 5 EO) | 3–9% |
| soap as fatty acid (e.g. lauric acid) | 0–3% |
| aminoethanol | 1–5% |
| sodium citrate | 5–10% |
| hydrotrope (e.g. sodium toluenesulfonate) | 2–6% |
| borate (as $B_4O_7$) | 0–2% |
| carboxymethylcellulose | 0–1% |
| ethanol | 1–3% |
| propylene glycol | 2–5% |
| enzymes | 0–5% |
| minor ingredients (e.g. polymers, dispersants, perfume, optical brighteners) | 0–5% |

11) An aqueous liquid detergent composition comprising

| | |
|---|---|
| linear alkylbenzenesulfonate (calculated as acid) | 20–32% |
| alcohol ethoxylate (e.g. $C_{12-15}$ alcohol, 7 EO or $C_{12-15}$ alcohol, 5 EO) | 6–12% |
| aminoethanol | 2–6% |
| citric acid | 8–14% |
| borate (as $B_4O_7$) | 1–3% |
| polymer (e.g. maleic/acrylic acid copolymer, anchoring polymers as e.g. lauryl methacrylate/acrylic acid copolymer and CMC) | 0–3% |
| glycerol | 3–8% |
| enzymes | 0–5% |
| minor ingredients (e.g. hydrotropes, dispersants, perfume, optical brighteners) | 0–5% |

12) A detergent composition formulated as a granulate having a bulk density of at least 600 g/l comprising

| | |
|---|---|
| anionic surfactant (linear alkylbenzenesulfonate, alkyl sulfate, alpha-olefinsulfonate, alpha-sulfo fatty acid methyl esters, alkanesulfonates, soap) | 25–40% |
| nonionic surfactant (e.g. alcohol ethoxylate) | 1–10% |
| sodium carbonate (as $Na_2CO_3$) | 8–25% |
| soluble silicates (as $Na_2O,2SiO_2$) | 5–15% |
| sodium sulfate (as $Na_2SO_4$) | 0–5% |
| zeolite (as $NaAlSiO_4$) | 15–28% |
| sodium perborate (as $NaBO_3.4H_2O$) | 0–20% |
| bleach activator (TAED or NOBS) | 0–5% |
| enzymes | 0–5% |
| minor ingredients (e.g. perfume, optical brighteners) | 0–3% |

13) Detergent formulations as described in 1)–12) where the content of linear alkylbenzenesulfonate—or a part of it—is substituted by alkyl sulfate ($C_{12}$–$C_{18}$).

14) Detergent formulations as described in 1)–13) which contain a stabilized or encapsulated peracid either as an additional component or as a substitute for already specified bleach systems.

15) Detergent compositions as described in 3), 7), 9) and 12) where the content of perborate is substituted by percarbonate.

16) Detergent composition formulated as a nonaqueous detergent liquid comprising a liquid nonionic surfactant as e.g. linear alkoxylated primary alcohol, a builder system (e.g. phosphate), enzyme and alkali. The detergent may also comprise anionic surfactant and/or a bleach system.

The lipase of the invention may be incorporated in concentrations conventionally employed in detergents. It is at present contemplated that, in the detergent composition of the invention, the lipase may be added in an amount corresponding to 50–10,000 LU per liter of wash liquor, preferably 100–2,000 LU/l, or 50–50,000 LU per gram of detergent, preferably 500–10,000 LU/g. The amount of lipase protein may be 0.001–100 mg per liter of wash liquor or 0.001–100 mg per gram of detergent.

Dishwashing Composition

The dishwashing detergent composition comprises a surfactant which may be anionic, non-ionic, cationic, amphoteric or a mixture of these types. The detergent will contain 0–90% of non-ionic surfactant such as low- to non-foaming ethoxylated propoxylated straight-chain alcohols.

The detergent composition may contain detergent builder salts of inorganic and/or organic types. The detergent builders may be phosphorus-containing and/or non-phosphorus-containing types. The detergent composition usually contains 1–90% of detergent builders.

Examples of phosphorus-containing inorganic alkaline detergent builders include the water-soluble salts especially alkali metal pyrophosphates, orthophosphates, polyphosphates, and phosphonates. Examples of non-phosphorus-containing inorganic builders include water-soluble alkali metal carbonates, borates and silicates as well as the various types of water-insoluble crystalline or amorphous alumino silicates of which zeolites are the best-known representatives.

Examples of suitable organic builders include the alkali metal, ammonium and substituted ammonium, citrates, succinates, malonates, fatty acid sulphonates, carboxymetoxy succinates, ammonium polyacetates, carboxylates, polycarboxylates, aminopolycarboxylates, polyacetyl carboxylates and polyhydroxsulphonates.

Other suitable organic builders include the higher molecular weight polymers and co-polymers known to have builder properties, for example appropriate polyacrylic acid, polymaleic and polyacrylic/polymaleic acid copolymers and their salts.

The dishwashing detergent composition may contain bleaching agents of the chlorine/bromine-type or the oxygen-type. Examples of inorganic chlorine/bromine-type bleaches are lithium, sodium or calcium hypochlorite and hypobromite as well as chlorinated trisodium phosphate. Examples of organic chlorine/bromine-type bleaches are heterocyclic N-bromo and N-chloro imides such as trichloroisocyanuric, tribromoisocyanuric, dibromoisocyanuric and dichloroisocyanuric acids, and salts thereof with water-solubilizing cations such as potassium and sodium. Hydantoin compounds are also suitable.

Oxygen bleaches are preferred, for example in the form of an inorganic persalt, preferably with a bleach precursor or as a peroxy acid compound. Typical examples of suitable peroxy bleach compounds are alkali metal perborates, both tetrahydrates and monohydrates, alkali metal percarbonates, persilicates and perphosphates. Preferred activator materials are TAED and glycerol triacetate.

The dishwashing detergent composition of the invention may be stabilized using conventional stabilizing agents for the enzyme(s), e.g. a polyol such as propylene glycol, a sugar or a sugar alcohol, lactic acid, boric acid, or a boric acid derivative, e.g. an aromatic borate ester.

The dishwashing detergent composition of the invention may also contain other conventional detergent ingredients, e.g. deflocculant material, filler material, foam depressors, anti-corrosion agents, soil-suspending agents, sequestering agents, anti-soil redeposition agents, dehydrating agents, dyes, bactericides, fluorescers, thickeners and perfumes.

Finally, the lipase of the invention may be used in conventional dishwashing detergents, e.g. any of the detergents described in any of the following patent publications:
EP 551670, EP 533239, WO 9303129, EP 507404, U.S. Pat. No. 5,141,664, GB 2247025, EP 414285, GB 2234980, EP 408278, GB 2228945, GB 2228944, EP 387063, EP 385521, EP 373851, EP 364260, EP 349314, EP 331370, EP 318279, EP 318204, GB 2204319, EP 266904, U.S. Pat. No. 5,213,706, EP 530870, CA 2006687, EP 481547, EP 337760, WO 93/14183, U.S. Pat. No. 5,223,179, WO 93/06202, WO 93/05132, WO 92/19707, WO 92/09680, WO 92/08777, WO 92/06161, WO 92/06157, WO 92/06156, WO 91/13959, EP 399752, U.S. Pat. No. 4,941,988, U.S. Pat. No. 4,908,148.

EXAMPLES

The following examples further illustrate the present invention, and they are not intended to be in any way limiting to the scope of the invention as claimed.

Example 1

Production of Lipase

Seed cultures were produced in shake flasks from each of the strains LB 501 (DSM 7349), LB 502 (DSM 7350), LB 511 (FERM BP-4236), and LB 512 (FERM BP-4237), respectively, in a Waksman medium of the following composition (g/liter):

| | |
|---|---|
| Glucose | 10 |
| Peptone | 5 |
| Meat Extract | 5 |
| NaCl | 5 |
| pH adjusted to 7.0 | |

After 2 days at 30° C. and 230 rpm, 5 ml of the seed culture was inoculated in shake flasks containing 100 ml of the following medium (g/liter):

| | |
|---|---|
| Pharmamedia ™ (supplied from Traders Protein, The Procter & Gamble Oilseed Products Co.) | 20 g |
| Corn steep powder | 10 g |
| Glycerol | 10 g |
| $K_2HPO_4$ | 1 g |
| $MgSO_4$, $7H_2O$ | 0.5 g |
| pH adjustment to 7.0 before autoclaving. | |
| Autoclaving 20 min./121° C. | |

Jojoba oil, 1 ml, was added to each shake flask, and the flasks were cultivated at 27° C. for 4 days at 230 rpm.

The culture broth was subjected to liquid/solid separation by centrifugation. The supernatant was freeze-dried, and a crude powder preparation as obtained.

Example 2

Production of Lipase

As indicated below, strains were cultivated in 250 ml shake flasks containing 100 ml of culture media denoted ACT-1, ACT-2, ACT-3, ACT-4 and ACT-5 having the following composition (ml/SF indicates ml per shake flask):

| | ACT-1 | ACT-2 | ACT-3 | ACT-4 | ACT-5 |
|---|---|---|---|---|---|
| Pharmamedia (g/l) | 20 | 20 | 20 | 20 | 20 |
| C.S.P. (g/l) | 10 | 10 | 10 | | 10 |
| N.Z. amine (g/l) | | | | 10 | |
| Glycerol (g/l) | 10 | 10 | 10 | 10 | 10 |
| $MgSO_4.7H_2O$ (g/l) | 0.5 | 0.5 | 0.5 | 0.5 | 0.5 |
| $K_2HPO_4$ (g/l) | 1 | 1 | 1 | 1 | 1 |
| Jojoba oil (ml/SF) | 1 | | 1 | 1 | 2 |
| Soybean oil (ml/SF) | | 2 | | | |
| Adjust to pH | 6.0 | 6.5 | 6.5 | 6.0 | 6.0 |

Each strain was cultivated at 27° C. for 4 days. At the end of the cultivation, pH and lipase activity (LU) of the culture broth were measured. One Lipase Unit (LU) is the amount of enzyme which, under standard conditions (i.e. at 30.0° C.; pH 7.0; and tributyrine substrate) liberates 1 μmol of titratable butyric acid per minute. Results:

| Species | Strain | Culture medium | pH after cultivation | LU/ml |
|---|---|---|---|---|
| S. griseus | LB 501 | ACT-1 | 8.1 | 8.0 |
| S. griseus | LB 502 | ACT-2 | 8.3 | 3.0 |
| S. griseus | LB 524 | ACT-1 | 8.3 | 3.5 |
| S. coelicolor | LB 511 | ACT-5 | 8.7 | 6.5 |
| S. coelicolor | LB 512 | ACT-3 | 8.2 | 6.4 |
| S. coelicolor | ATCC 23899 | ACT-1 | 8.6 | 4.5 |
| S. parvus | ATCC 12433 | ACT-1 | 8.4 | 3.1 |

Example 3

Production of Lipase

As indicated below, strains were cultivated in shake flasks containing culture medium ACT-1 (described in Example 2) at 27° C. The pH and lipase activity of the culture broth were measured after 3, 4 and 5 days. The results were as follows:

| Species | Strain | Day | LU activity | pH |
|---|---|---|---|---|
| S. griseus | LB 502 (DSM 7350) | 3 | 10.6 | 8.3 |
| | | 4 | 10 | 8.7 |
| | | 5 | 10 | 8.9 |
| S. coelicolor | ATCC 23899 | 3 | 5.2 | 6.8 |
| | | 4 | 6.1 | 8.0 |
| | | 5 | 2.6 | 8.6 |
| S. limosus | ATCC 19778 | 3 | 0.6 | 7.1 |
| | | 4 | 1.5 | 7.1 |
| | | 5 | 2.2 | 7.5 |
| S. alboviridis | ATCC 25425 | 3 | 1.8 | 8.1 |
| | | 4 | 4.6 | 8.4 |
| | | 5 | 5.2 | 8.8 |
| S. griseus | ATCC 23345 | 3 | 2.1 | 7.9 |
| | | 4 | 2.9 | 8.1 |
| | | 5 | 7.0 | 8.3 |
| S. parvus | ATCC 12433 | 4 | 0.6 | 8.1 |
| | | 5 | 1.2 | 8.2 |
| S. setonii | ATCC 25497 | 3 | 35 | 7.6 |
| | | 4 | 56 | 7.9 |
| | | 5 | 72 | 8.3 |
| S. nitrosporeus | ATCC 12769 | 3 | 0.5 | 7.4 |
| | | 4 | 0.2 | 7.9 |
| | | 5 | 0.7 | 8.0 |

Example 4

Lipase Production from S. griseus LB 502 (DSM 7350)

The strain was cultivated at 27° C. in shake flasks on a medium having the following composition:

| | |
|---|---|
| Pharmamedia | 20 g/l |
| Corn steep powder | 6.64 g/l |
| Glycerol | 10 g/l |
| $K_2HPO_4$ | 1 g/l |
| $MgSO_4.7H_2O$ | 0.5 g/l |
| Jojoba oil | 1 ml/shake flask |
| pH adjusted to | 6.0 |

After 4 days, the yield was approx. 30 LU/ml.

Example 5

Purification of Lipase

Crude lipase from S. griseus LB 501 (DSM 7349) was purified by hydrophobic chromatography followed by ion exchange chromatography, as follows.

Hydrophobic chromatography: Crude lipase powder prepared in Example 1 was dissolved and adjusted to 3.5M $CH_3COONH_4$. This was applied to a column of t-Butyl Macropep HIC (product of Biorad), and the column was washed with the same concentration of $CH_3COONH_4$ to remove most of the color and protein. Afterward a gradient was started, first rapidly down to 1M, then slowly down to 0M. Two peaks were seen in the chromatogram, and accordingly two pools of lipase were collected. The total recovery of lipase activity was over 80%.

Ion exchange chromatography: After concentrating and deionizing by ultrafiltration (recovery 60–70%, due to high viscosity), each pool was applied to a column of DEAE-Toyopearl. One broad peak containing lipase activity was seen on the chromatogram and was collected. Some color was removed, and the recovery of lipase activity was over 80%. Finally, each pool was again ultrafiltered (recovery over 80%).

The starting material had a total lipase activity of 16,500 LU. Pools 1 and 2 had specific lipase activities of 74.4 LU/mg protein and 43.3 LU/mg protein, and total lipase activities of 3350 LU and 1860 W, respectively. Thus, the over-all recovery of lipase activity was 32%.

Both pools were found to contain at least two lipases having isoelectric points (by isoelectric focusing) of 5.5 or lower and molecular weights between 28 and 43 kD.

Example 6 pH Activity Curves of Lipase Preparations pH profiles were determined for lipase preparations from the following strains:

S. griseus LB 501 (DSM 7349)
S. griseus LB 502 (DSM 7350)
S. coelicolor LB 511 (FERM BP-4236)
S. coelicolor LB 512 (FERM BP-4237)
S. griseus LB 524 (DSM 8672)
S. coelicolor N 2293 (ATCC 23899)
S. parvus N 2300 (ATCC 12433)

The pH profiles of lipase preparations were determined in the absence of $Ca^{++}$ at 40° C. with olive oil as substrate and PVA as emulsifier at 20 minutes reaction time, using glycine buffer at pH 8.5–10.5. The results are presented in FIGS. 1–7 as relative activity (% rel.) against pH.

It is seen that the lipases have optimum activity in the absence of $Ca^{++}$ at about pH 9–10 and that they have more than 50% of the optimum activity at pH 10.

Example 7

Lipase Activity at Alkaline pH

Lipase preparations were tested for lipase activity at pH 6–10 by a diffusion plate technique.

The lipase preparations obtained after 3 and 4 days cultivation in Example 3 were tested. Diffusion plates were prepared as described in Example 11 of WO 88/02775 with a test medium containing olive oil and PVA at pH 6, 8.5 and 10, respectively, and the presence or absence of lipase activity at the pH of the medium was determined from the appearance of a clearing zone.

The results showed that all lipase preparations from Example 3 displayed activity at pH 6, 8.5 and 10, i.e. they are all active at high pH up to pH 10.

Example 8

Positional Specificity

The positional specificity was determined by hydrolysis of triglyceride and analysis of the diglycerides formed with a lipase preparation of the invention.

A lipase preparation from S. griseus LB 502 (DSM 7350) was used to hydrolyze olive oil as substrate with PVA as emulsifier at pH 10 in glycine buffer for 30 minutes at pH 10, whereafter the hydrolysis products were analyzed by latroscan. Lipolase, a prior-art positionally specific lipase preparation derived from Humicola lanuginosa, was used for comparison.

Figure 1:
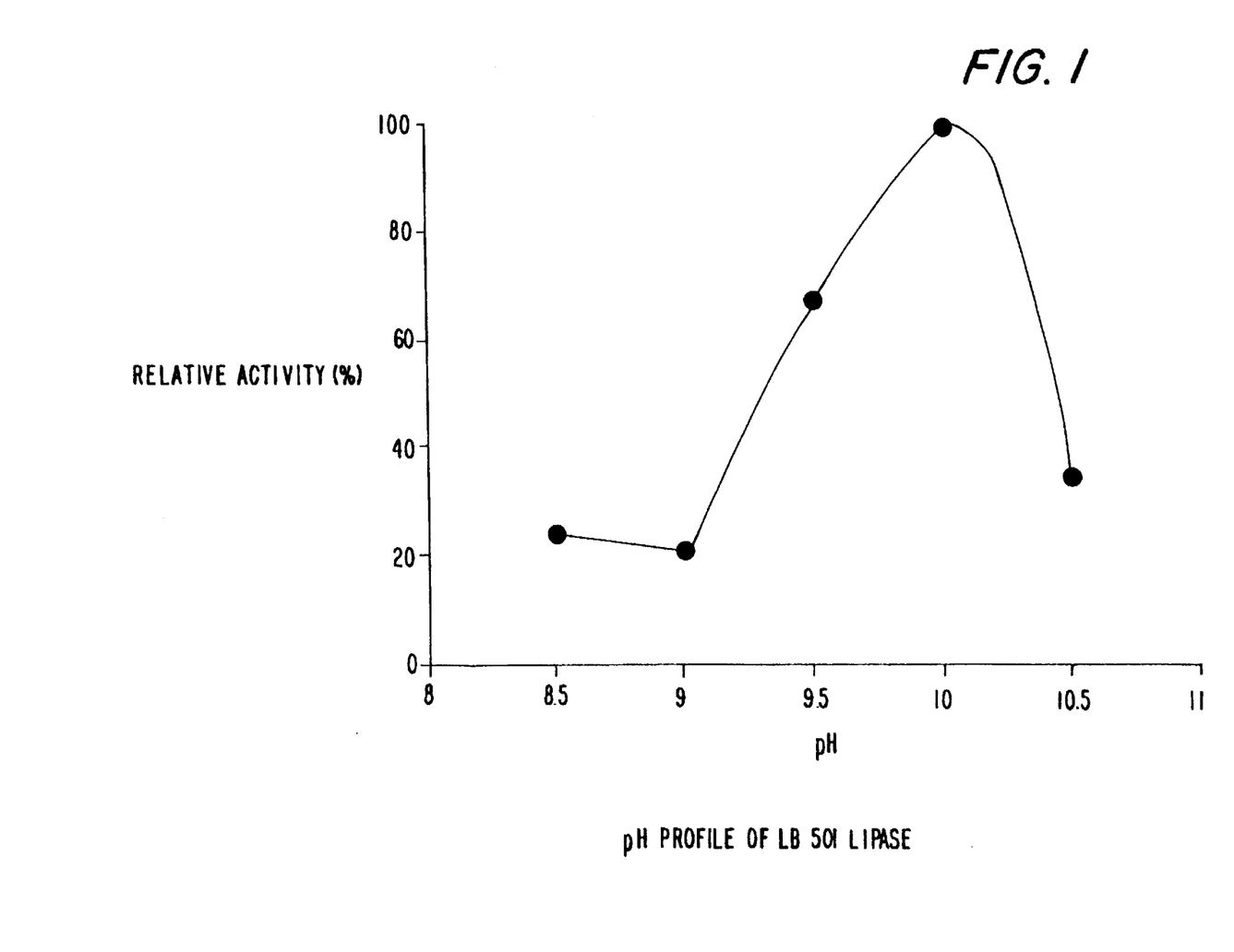
FIGS. 1–7 shows pH profiles for the activity of lipase preparations of the invention derived from the following strains: *S. griseus* LB 501 (DSM 7349), *S. griseus* LB 502 (DSM 7350), *S. coelicolor* LB 511 (FERM BP-4236), *S. coelicolor* LB 512 (FERM BP-4237), *S. griseus* LB 524 (DSM 8672), *S. coelicolor* N 2293 (ATCC 23899) and *S. paivus* N 2300 (ATCC 12433). Further details are given in Example 6.
Figure 2:
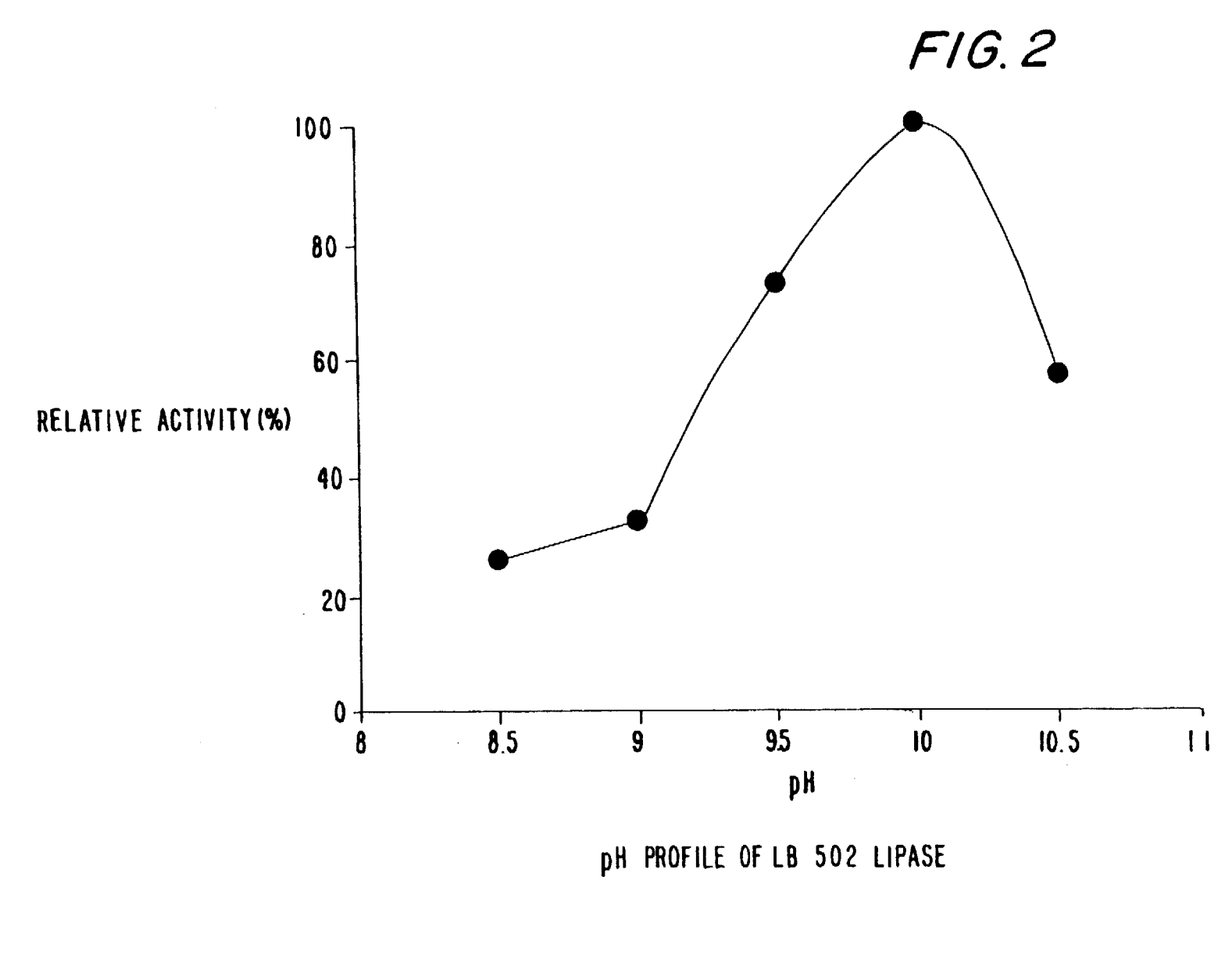
Figure 3:
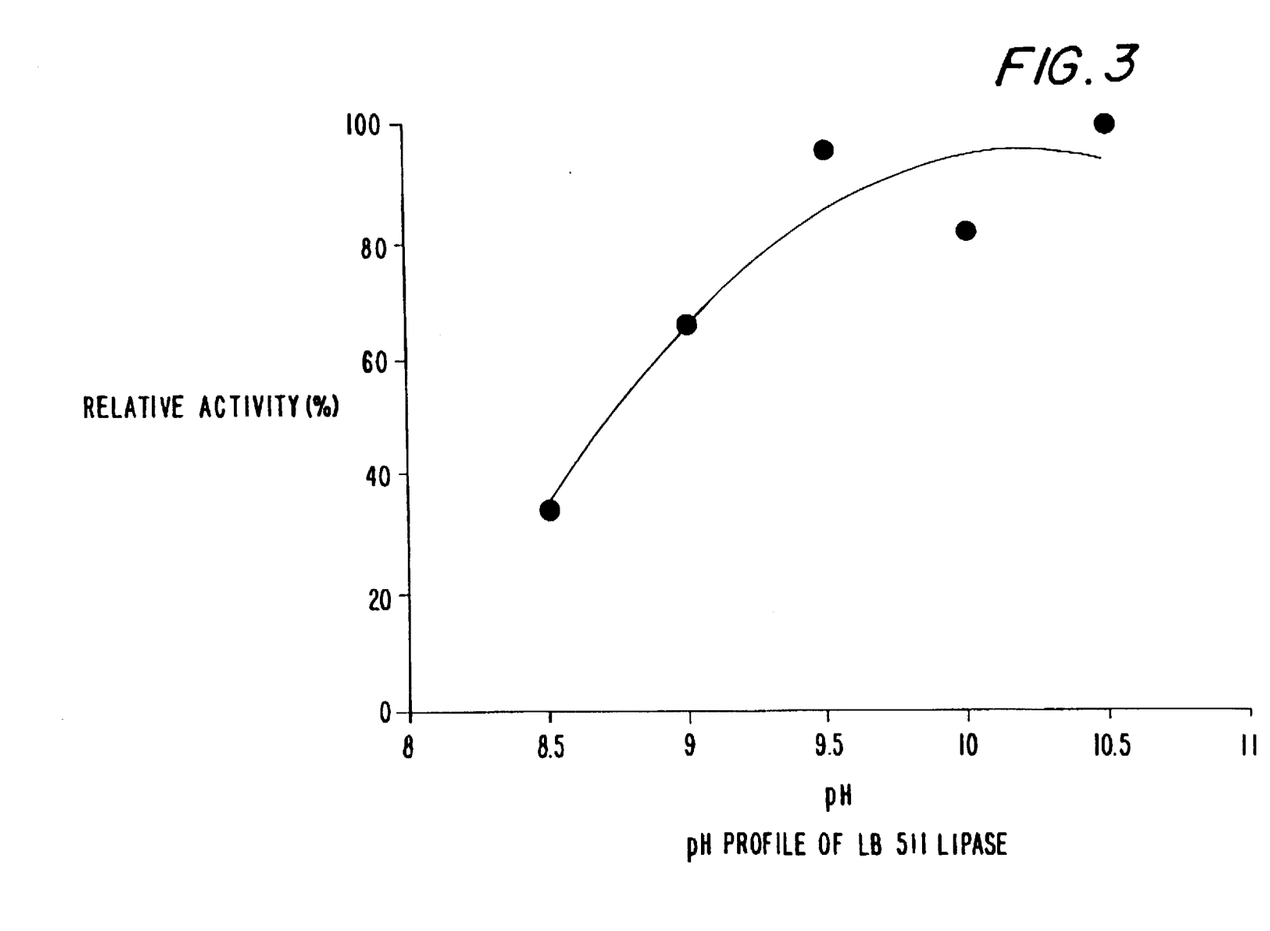
Figure 4:
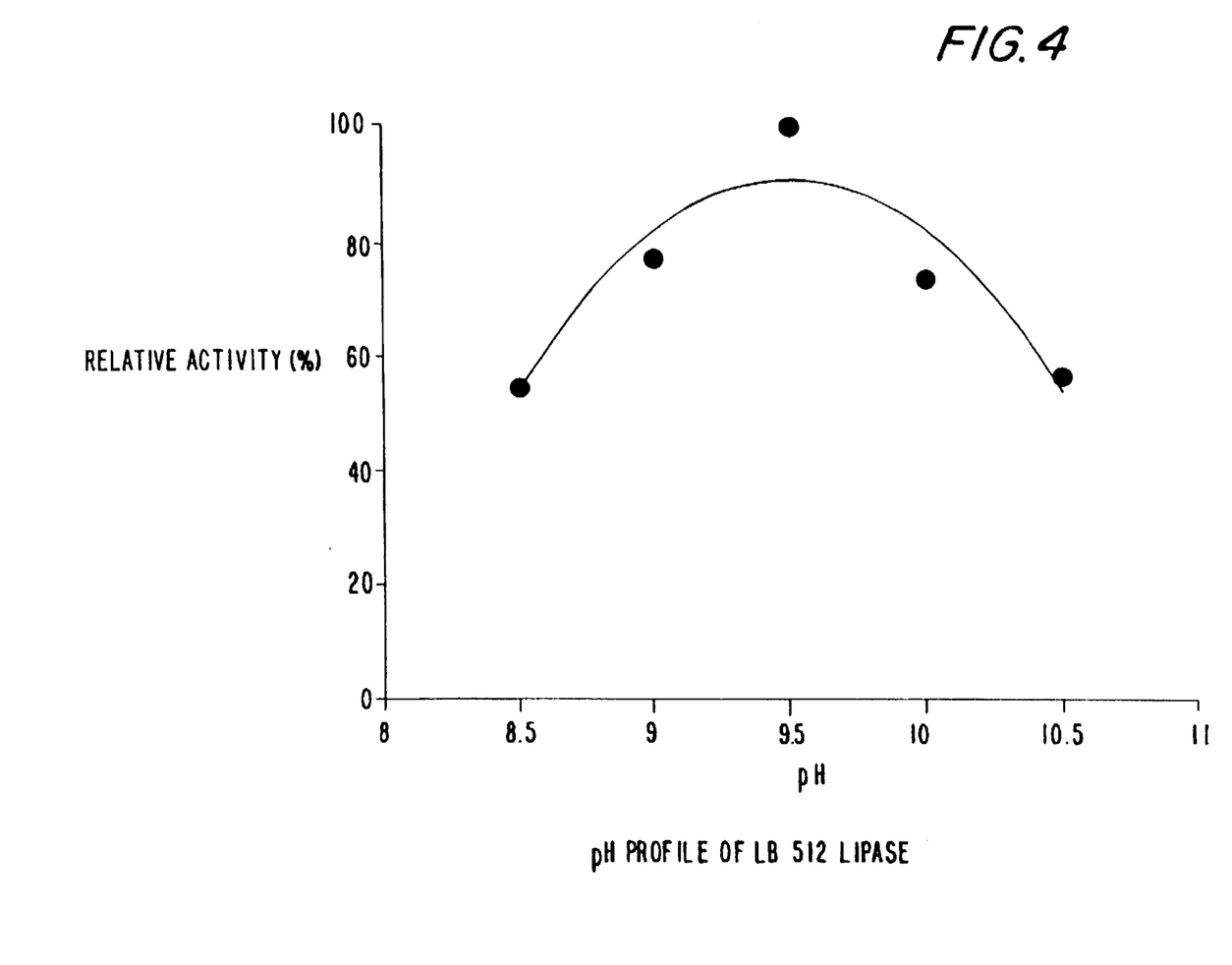
Figure 5:
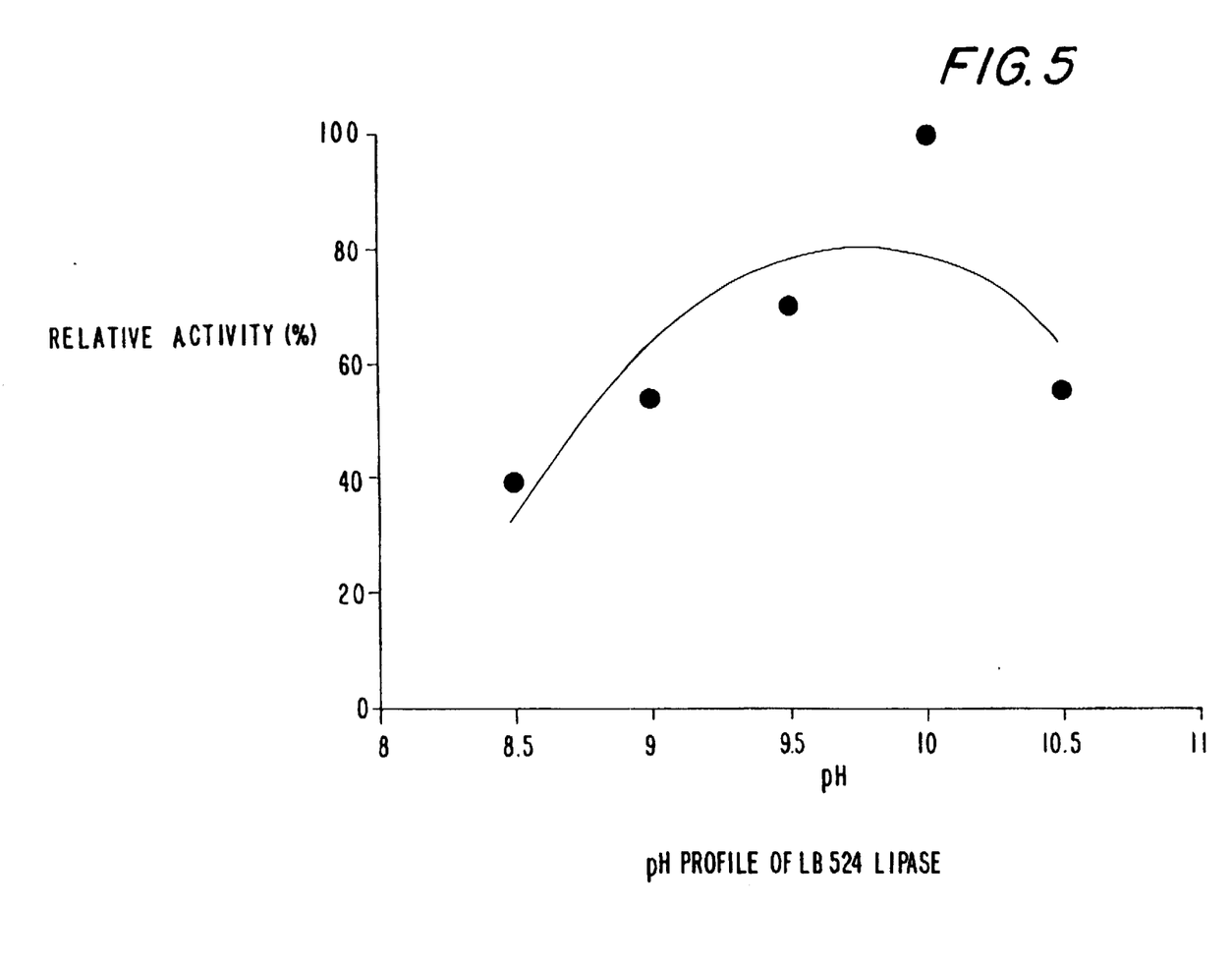
Figure 6:
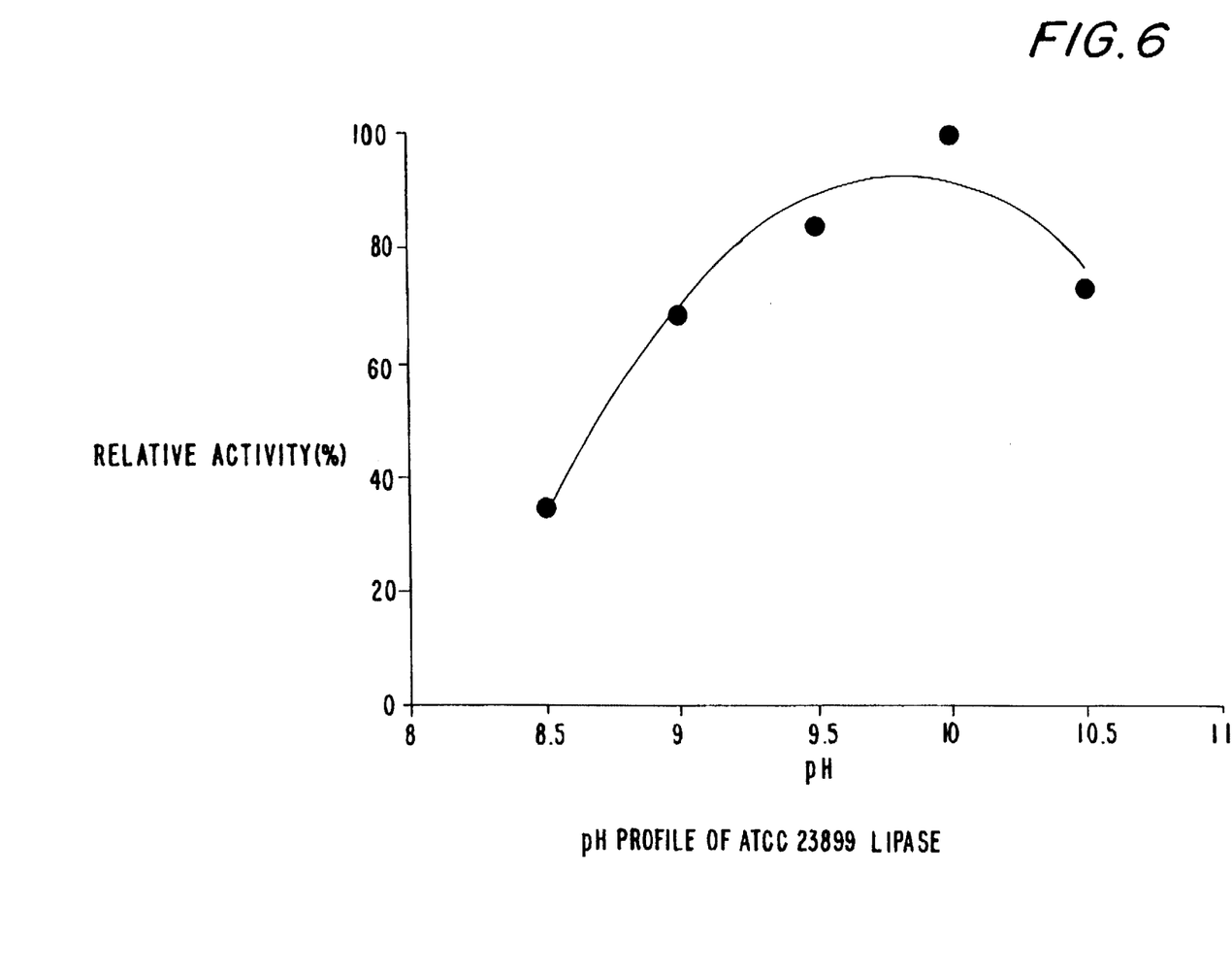
Figure 7:
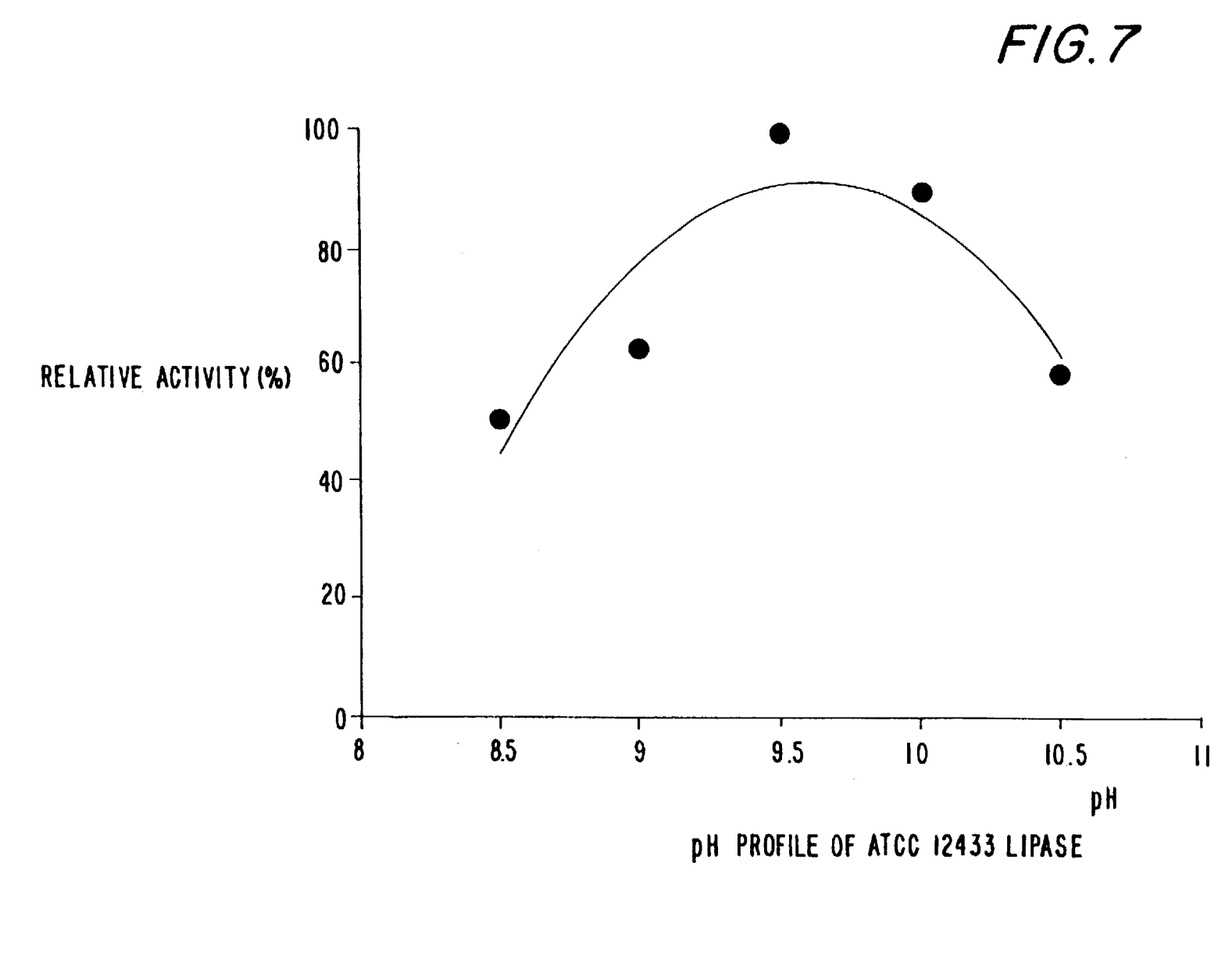
Figure 8A:
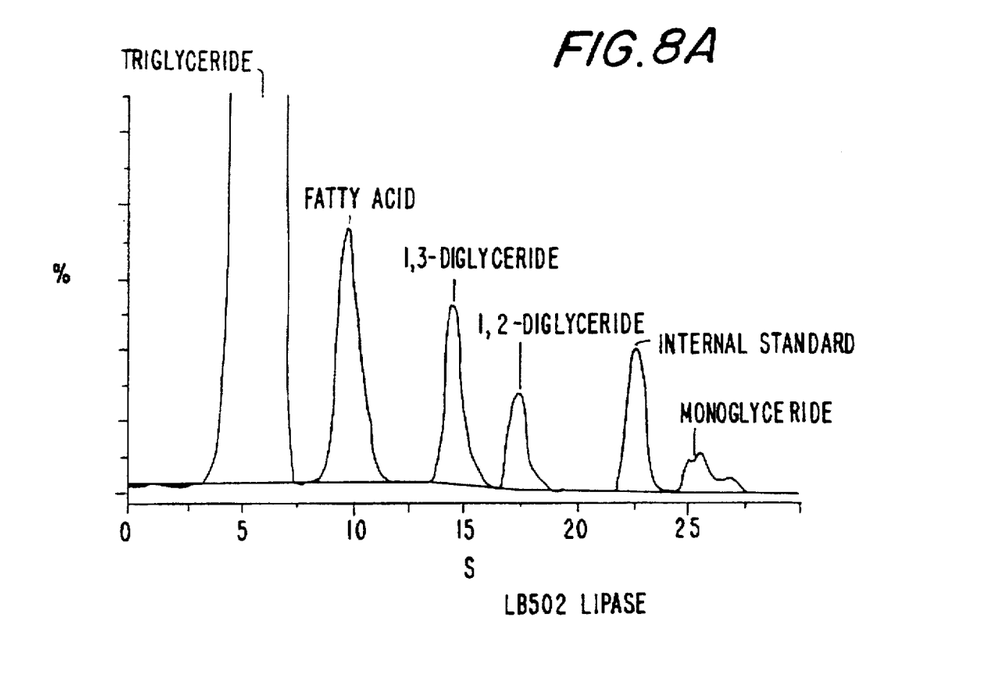
FIG. 8 shows chromatograms from Iatroscan after hydrolysis of olive oil with a lipase preparation of the invention (from LB 502) and a prior-art positionally specific lipase (Lipolase). Further details are given in Example 8.
Figure 8B:
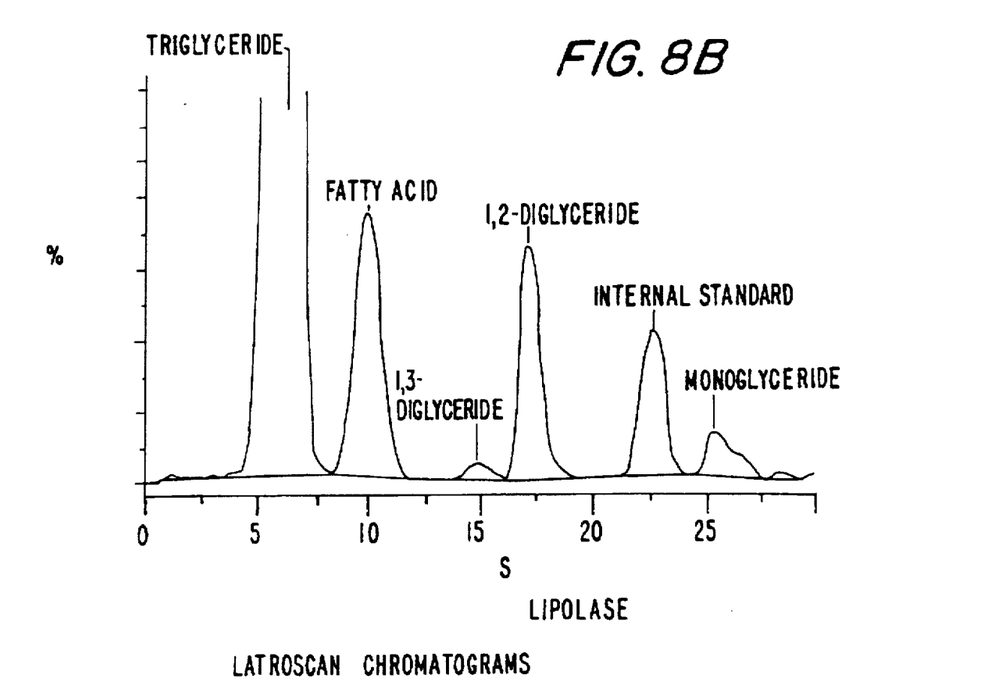

The results are shown in FIG. 8. It is seen that with the lipase preparation of the invention, more 1-3-diglyceride was formed than 1,2-diglyceride, indicating that the preparation is positionally non-specific, with higher activity at the 2-position than the 1- and 3-positions of the triglyceride. Lipolase gave almost no formation of 1,3-diglyceride, confirming that it is positionally specific, i.e. it reacts only in the 1- and 3-positions of the triglyceride.

Lipase preparations of the invention from S. griseus LB 524 (DSM 8672), S. coelicolor N 2293 (ATCC 23899) and S. parvus N 2300 (ATCC 12433) produced similar results as LB 502.

Example 9

Effect of Detergent on Lipase Activity

The lipase activity of various lipase preparations was measured in the presence of 0.1% of a nonionic or anionic surfactant (alcohol ethoxylate or linear alkylbenzene sulfonate) at pH 7.5 and compared with a control without detergent.

The lipase preparations of Example 2 were used. In each test, 0.1 ml of lipase solution was mixed with 0.4 ml of a 1.0 mM solution of p-nitrophenyl butyrate in 0.2M Tris-HCl (pH 7.5) and 0.5 ml of a 0.2% detergent solution. A 20 control was made with water instead of the detergent solution. The mixture was incubated at 40° C. for 30 minutes, and the extent of hydrolysis was determined by measuring the optical density at 415 nm.

The results are expressed as relative activity in the presence of detergent compared to the control.

| Species | Strain | Relative activity in detergent | |
|---|---|---|---|
| | | Alcohol ethoxylate | Linear alkylbenzene sulfonate |
| S. griseus | LB 501 (DSM 7349) | 55% | 75% |
| S. griseus | LB 502 (DSM 7350) | >100% | >100% |
| S. griseus | LB 524 (DSM 8672) | 100% | 97% |
| S. coelicolor | LB 511 (FERM BP-4236) | 100% | 21% |
| S. coelicolor | LB 512 (FERM BP-4237) | 87% | 50% |
| S. coelicolor | ATCC 23899 | 95% | 75% |
| S. parvus | ATCC 12433 | 97% | >100% |

It is seen that in the presence of alcohol ethoxylate, all lipase preparations retain more than 50% of their activity, most retain more than 75%, and some retain more than 90%. In the presence of linear alkylbenzene sulfonate, most lipase preparations retain at least 50% of their activity, most of these retain at least 75%, and some retain more than 90%.

Example 10

Lipase Activity in Detergent

The lipase activity of various lipase preparations was measured in the a solution of a built detergent at high pH and compared with a control without detergent.

In each test, the lipase preparation was added to a detergent solution of the following composition (indicated as active material). The mixture was incubated with olive oil as substrate and PVA as emulsifier at 40° C. for 60 minutes, whereafter the amount of free fatty acid formed was determined. A control was made with glycine or diethanol buffer at the same pH instead of the detergent solution.

| | |
|---|---|
| Linear alkylbenzene sulfonate (Nansa 1169/P) | 0.35 g/l |
| Alcohol ethoxylate (Dobanol 25-7) | 0.15 g/l |
| Sodium tripolyphosphate (STPP) | 1.25 g/l |
| Sodium sulfate | 1.00 g/l |
| Sodium carbonate | 0.45 g/l |
| Sodium metasilicate | 0.15 g/l |
| pH | 10.2 |

The results are expressed as relative activity in the presence of detergent compared to the control.

| Species | Strain | Relative activity in detergent solution | Buffer used in control |
|---|---|---|---|
| S. griseus | LB 502 (DSM 7350) | 67% | diethanol amine |
| S. griseus | LB 524 (DSM 8672) | 76% | glycine |
| S. coelicolor | ATCC 23899 | 96% | diethanol amine |
| S. parvus | ATCC 12433 | 73% | diethanol amine |

It is seen that the above lipase preparations have a relative activity of more than 50% in the detergent solution compared to the control.

Example 11

Effect of $Ca^{++}$ on Lipase Activity

The activity of a lipase preparation of the invention was measured without addition of $Ca^{++}$ and with addition of various amounts of $Ca^{++}$.

A lipase preparation from S. griseus LB 502 (DSM 7350) was incubated with olive oil as substrate and PVA as emulsifier at 40° C. for 10 minutes in a diethanol amine buffer at pH 10, whereafter the extent of hydrolysis was determined. The experiment was repeated with addition of a calcium salt in various concentrations.

Figure 9:
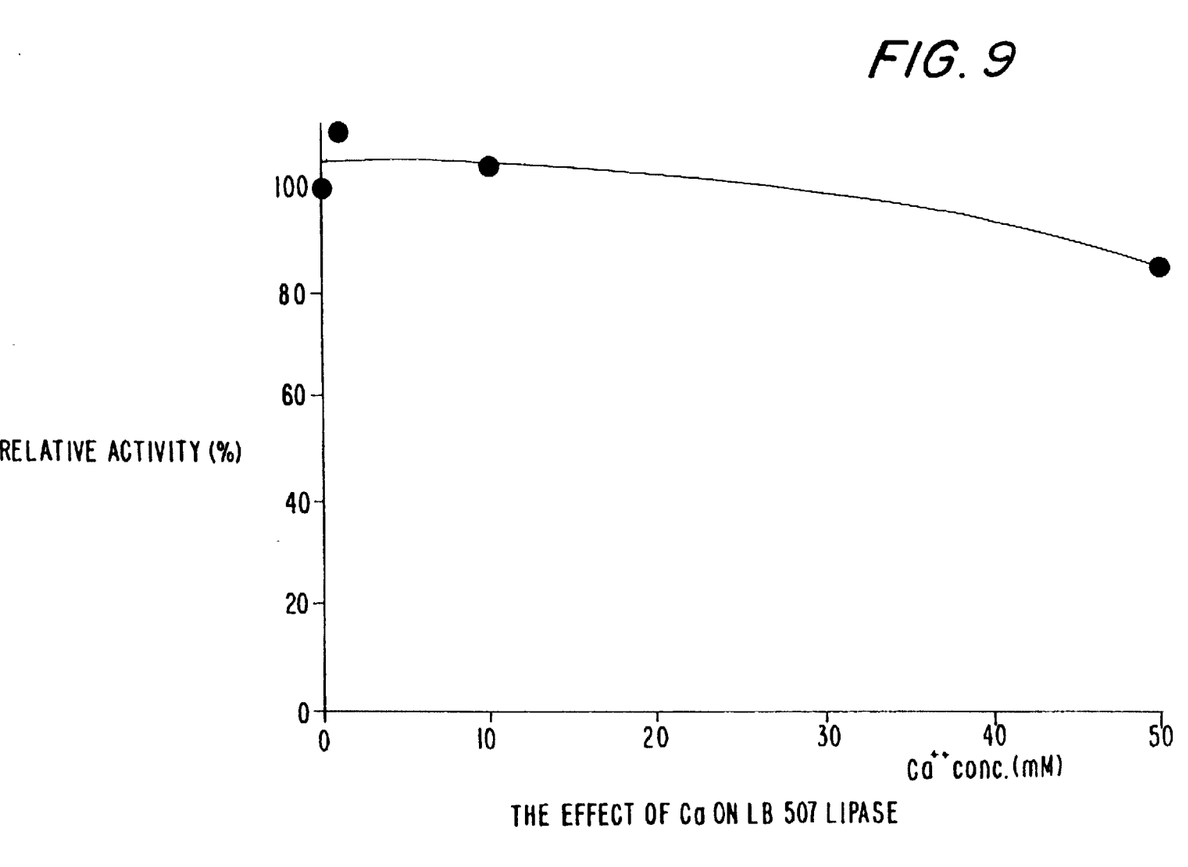
FIG. 9 shows the effect of $Ca^{++}$ addition on the activity of a lipase preparation of the invention. Further details are given in Example 11.

The results are shown in FIG. 9. It is seen that the lipase activity of this preparation does not decrease when the $Ca^{++}$ concentration is lowered.

We claim:

1. A purified lipase which:
   (1) is positionally non-specific,
   (2) is active on olive oil,
   (3) has a pH optimum of at least 9, when determined in a $Ca^{++}$ free assay with olive oil as substrate and polyvinyl alcohol as emulsifier at 40° C. for 20 minutes, and
   (4) is obtained from a strain of Streptomyces alboviridis, Streptomyces coelicolor, Streptomyces griseus, Streptomyces linosus, Streptomyces nitrosporeus, Streptomycesparvus, Streptomyces setonii.

2. The lipase according to claim 1, wherein the pH optimum is in the range of 9–11.

3. The lipase according to claim 2, wherein the pH optimum is in the range of 9.5–10.5.

4. The lipase according to claim 1 which has an activity at pH 10 which is more than 50% of the activity at the pH optimum, when both activities are determined in the $Ca^{++}$ free assay.

5. The lipase according to claim 1 which has an activity in the absence of $Ca^{++}$ which is more than 50% of the activity at 50 mM $Ca^{++}$ when both activities are measured with olive oil as substrate and polyvinyl alcohol as emulsifier at pH 10.

6. The lipase according to claim 1 which has an activity in a detergent solution at pH 10.2 which is more than 50% of the activity in diethanol amine buffer at pH 10, when both activities are measured with olive oil as substrate and polyvinyl alcohol as emulsifier at 60 minutes reaction time, wherein the detergent solution consists of 0.35 g/l linear alkyl benzene sulfonate, 0.15 g/l alcohol ethoxylate, 1.25 g/l sodium tripolyphosphate, 1.00 g/l sodium sulfate, 0.45 g/l sodium carbonate and 0.15 g/l sodium metasilicate.

7. The lipase according to claim 1, wherein the strain is a strain of Streptomyces coelicolor.

8. The lipase according to claim 7, wherein the strain is selected from the group consisting of FERM BP-4236, FERM BP-4237, and ATCC 23899.

9. The lipase according to claim 1, wherein the strain is a strain of Streptomyces griseus.

10. The lipase according to claim 9, wherein the strain is selected from the group consisting of ATCC 23345, DSM 7349, DSM 7350, and DSM 8672.

11. The lipase according to claim 10, wherein the strain is DSM 7350.

12. The lipase according to claim 1, wherein the strain is a strain of Streptomyces parvus.

13. The lipase according to claim 12, wherein the strain is ATCC 12433.

14. The lipase according to claim 1, wherein the strain is a strain of Streptomyces alboviridis, Streptomyces linosus, Streptomyces nitrosporeus, Streptomyces setonii.

15. The lipase according to claim 14, wherein the strain is Streptomyces alboviridis ATCC 25425, Streptomyces linosus ATCC 19778, Streptomyces nitrosporeus ATCC 27472 or Streptomyces setonii ATCC 25497.

16. The lipase according to claim 1 which is in the form of a non-dusting granulate, a stabilized liquid, a slurry, or a protected enzyme.

17. A strain of *Streptomyces griseus* which is capable of producing the lipase of claim 1.

18. A process for producing a lipase according to claim 1, comprising (a) cultivating a lipase-producing strain of *Streptomyces alboviridis, Streptomyces coelicolor, Streptomyces griseus, Streptomyces linosus, Streptomyces nitrosporeus, Streptomyces parvus, Streptomyces setonii* in a suitable nutrient medium containing carbon and nitrogen sources and inorganic salts; and (b) recovering the lipase.

19. A detergent composition comprising a surfactant and a lipase according to claim 1.

20. The detergent composition according to claim 19, wherein the pH optimum is in the range of 9–11.

21. The detergent composition according to claim 19, wherein the lipase has an activity at pH 10 which is more than 50% of the activity at the pH optimum, when both activities are determined in the $Ca^{++}$ free assay.

22. The detergent composition according to claim 19, wherein the lipase has an activity in the absence of $Ca^{++}$ which is more than 50% of the activity at 50 mM $Ca^{++}$ when both activities are measured with olive oil as substrate and polyvinyl alcohol as emulsifier at pH 10.

23. The detergent composition according to claim 19, wherein the lipase has an activity in a detergent solution at pH 10.2 which is more than 50% of the activity in diethanol amine buffer at pH 10, when both activities are measured with olive oil as substrate and polyvinyl alcohol as emulsifier at 60 minutes reaction time, wherein the detergent solution consists of 0.35 g/l linear alkyl benzene sulfonate, 0.15 g/l alcohol ethoxylate, 1.25 g/l sodium tripolyphosphate, 1.00 g/l sodium sulfate, 0.45 g/l sodium carbonate and 0.15 g/l sodium metasilicate.

24. The detergent composition according to claim 19, wherein the strain is a strain of *Streptomyces coelicolor*.

25. The detergent composition according to claim 24, wherein the strain is selected from the group consisting of FERM BP-4236, FERM BP-4237, and ATCC 23899.

26. The detergent composition according to claim 19, wherein the strain is a strain of *Streptomyces griseus*.

27. The detergent composition according to claim 26, wherein the strain is selected from the group consisting of ATCC 23345, DSM 7349, DSM 7350, and DSM 8672.

28. The detergent composition according to claim 27, wherein the strain is DSM 7350.

29. The detergent composition according to claim 19, wherein the strain is a strain of *Streptomyces parvus*.

30. The detergent composition according to claim 29, wherein the strain is ATCC 12433.

31. The detergent composition according to claim 19, wherein the strain is a strain of *Streptomyces alboviridis, Streptomyces linosus*, or *Streptomyces nitrosporeus, Streptomyces setonii*.

32. The detergent composition according to claim 31, wherein the strain is *Streptomyces alboviridis* ATCC 25425, *Streptomyces linosus* ATCC 19778, *Streptomyces nitrosporeus* ATCC 27472 or *Streptomyces setonii* ATCC 25497.

* * * * *